United States Patent [19]

Kokusho et al.

[11] 4,283,494

[45] Aug. 11, 1981

[54] MICROBIAL LIPASE, PROCESS FOR ITS PREPARATION AND MICROBIOLOGICALLY PURE CULTURE THEREFOR

[75] Inventors: Yoshitaka Kokusho, Kunitachi; Haruo Machida; Shinjiro Iwasaki, both of Hino, all of Japan

[73] Assignee: Meito Sangyo Kabushiki Kaisha, Japan

[21] Appl. No.: 900,234

[22] Filed: Apr. 26, 1978

[51] Int. Cl.$^3$ .................. C12N 9/20; C12N 1/20; C12R 1/05
[52] U.S. Cl. ................... 435/198; 435/19; 435/253; 435/829
[58] Field of Search ............... 435/198, 19, 829, 253

[56] References Cited

FOREIGN PATENT DOCUMENTS

| | | |
|---|---|---|
| 44-10754 | 5/1969 | Japan . |
| 46-29787 | 8/1971 | Japan . |
| 50-17559 | 5/1974 | Japan . |
| 52-21387 | 2/1977 | Japan ........................ 435/198 |

OTHER PUBLICATIONS

Yamaguchi et al., Agr. Biol. Chem., 37 (5), 999–1005, 1973.
Horiuti et al., J. Biochem, 81, 1639–1649 (1977).
Abstract of Papers at the 1977 Annual Meeting of the Agricultural Chemical Society of Japan, Abstract B-20.
Abstract of Papers at the 1974 Annual Meeting of the Agricultural Chemical Society of Japan, Abstract 2J-18.
Yakuzaigaku ("Pharmaceutical Science"), vol. 27, No. 4, p. 32 (314).
Eisei Kagaku, ("Hygienic Chemistry"), vol. 13, (1967), pp. 257–260.

*Primary Examiner*—Lionel M. Shapiro
*Attorney, Agent, or Firm*—Wenderoth, Lind & Ponack

[57] ABSTRACT

A microbial lipase which has (i) an optimal pH for activity of about 9±0.5, (ii) an optimal temperature for activity of about 40° C. to about 48° C., (iii) a lipase activity to be activated by bile salts, (iv) a cholesterol esterase activity, and (v) a molecular weight of about $30 \times 10^4$ to about $40 \times 10^4$; a process for its preparation; and microbiologically pure culture therefor.

11 Claims, 4 Drawing Figures

MICROBIAL LIPASE, PROCESS FOR ITS PREPARATION AND MICROBIOLOGICALLY PURE CULTURE THEREFOR

This invention relates to a microbial lipase capable of being activated with bile salts, which has characteristics not described in the literature; to a process for preparing it; and to a biologically pure culture useful for the production of the microbial lipase.

The term "microbial lipase," as used herein, denotes a lipase produced by a microorganism.

The microbial lipase in accordance with this invention is characterized by having (i) an optimal pH for activity of about 9±0.5,
(ii) an optimal temperature for activity of about 40° C. to about 48° C.,
(iii) a lipase activity to be activated by bile salts,
(iv) a cholesterol esterase activity, and
(v) a molecular weight of about $30 \times 10^4$ to about $40 \times 10^4$.

Processes for producing microbial lipase utilizing a host of microorganisms, especially bacteria, have been known heretofore, and for example, microorganisms belonging to the genus Pseudomonas, Chromobacterium, Achromobacterium, Staphylococcus, Brevibacterium, and Corynebacterium are used in such processes.

The present inventors made extensive investigations in an attempt to develop a lipase having an optimal pH for activity in the alkaline region and capable of being activated with bile salts. These investigations led to the discovery that Alcaligenes sp. PL-266 Meito Strain FERM-P No. 3187 (deposited at Fermentation Research Institute, Agency of Industrial Science & Technology, Japan), a microorganism belonging to the genus Alcaligenes, which the present inventors had separated from soil, has the ability to produce a lipase which has an optimal pH for activity in the alkaline region and is capable of being activated with bile salts. They applied it for a patent (Japanese Laid-Open Patent Publication No. 21387/77) and disclosed its microbiological characteristics and the enzymic characteristics of the lipase produced.

On further investigation, the present inventors isolated different species of the same genus from the soil in the outskirt of Tokyo, Japan. They subsequently found that this microorganism has the ability to produce a lipase which has an optimal pH for activity in the alkaline region and can be activated with bile salts, but is of different type from, and is more useful than, the lipase disclosed in the earlier patent application. They also succeeded in separating the lipase produced by this new strain. This new type of lipase has a cholesterol esterase activity not possessed by the lipase previously disclosed in addition to having a lipase activity. Because of this activity, it is also useful as a diagnostic reagent for various purposes, for example for determining cholesterol levels.

The amount of lipase produced by the newly found microorganism is, for example, as large as about 2,000 units/ml of the filtrate of the culture broth, and is far larger than the amount of lipase produced by the microorganisms disclosed in the earlier patent application which is about 320 units/ml of the filtrate of the culture broth.

Accordingly, the present invention contributes further to the technological field relating to lipase which have an optimal pH in the alkaline region, and which when orally administered to man or other animals as a digestant for example, will be activated with bile in the intestine (alkaline intestinal juice).

It is a primary object of this invention to provide a new type of microbial lipase which has the unique advantages and is not described in the literature.

Another object of this invention is to provide a process for producing the microbial lipase.

Still another object of this invention is to provide a biologically pure culture useful for the production of the microbial lipase.

The above and other objects and advantages of this invention will become more apparent from the following description.

Alcaligenes sp. PL-679 Meito strain useful for producing the microbial lipase of this invention is deposited at Fermentation Research Institute, Agency of Industrial Science & Technology, Japan under the deposit number FERM-P No. 3783. The same strain is deposited at American Type Culture Collection, U.S.A. under the deposit number ATCC 31371. The strain is also deposited in German Collection of Micoorganisms, Germany under the deposit number DSM 1239.

The microbiological properties of Alcaligenes sp. PL-679 Meito strain are as follows:

A. Morphological Characteristics

Rods, 0.5 to 0.7 by 1.0 to 4.0 μm, occurring singly, and occasionally in chains of 2 to 4 cells on nutrient agar medium or in nutrient broth.

Not pleomorphic.

Motile by means of 1 to 6 peritrichous flagella.

Spore not formed.

Gram-negative. Growth abundant and red colony formed on crystal violet agar.

Not acid-fast.

B. Cultural characteristics

Nutrient agar colonies: Circular, rough, lacerate, translucent, yellowish brown, center brown. Diffusible pigment not produced.

Nutrient agar slant: Spreading or echinulate, translucent, resinous, orange to yellowish brown.

Nutrient broth: Growth abundant, yellowish-brown, turbid with pellicle and sediment.

Gelatin stab: Filiform, no liquefaction. Growth abundant, yellowish brown on medium surface.

Litmus milk: Alkaline. No peptonization.

Potato: Growth abundant, orange, becoming light brown.

C. Physiological characteristics

Nitrites produced from nitrates.

No gas produced in nitrate broth under anaerobic conditions.

Methyl red test negative.

Voges-Proskauer test negative.

Indol not produced.

Hydrogen sulfide produced.

Starch not hydrolyzed.

Citrates utilized as sole sources of carbon (Koser's agar and Christensen's agar).

Nitrates and ammonium salts utilized as sole sources of nitrogen.

Diffusible pigment is not produced on nutrient agar, nutrient gelatin or potato dextrose agar. Diffusible faint brown pigment is produced on King A agar and Czapek-Dox agar. Diffusible faint yellowish brown pigment is produced on King B agar.

Urease not produced.
Oxidase positive.
Catalase positive.
pH range for growth: Growth between 5.5 and 11.0. No growth below 5.0 or above 12.0.
Temperature range for growth: Growth between 5° and 40° C. Optimal growth between 15° and 35° C.
Aerobic.
OF test: Neither acid nor gas is produced both in open and closed tubes.
From D-fructose and glycerol, acid (latent) but no gas produced in oxidation-fermentation medium of high and Leifson in open tubes. Neither acid nor gas produced from L-arabinose, D-xylose, D-glucose, D-mannose, D-galactose, maltose, sucrose, lactose, trehalose, D-sorbitol, D-mannitol, inositol or starch in open and closed tubes.

D. Other characteristics

Lipase produced.
3-Ketolactose is not produced.
Ammonia produced weakly from arginine.
The G+C content of DNA: 66.7 moles%

The taxonomical status of the present strain having the above microbiological characteristics has been investigated with reference to Bergey's Manual of Determinative Bacteriology, 8th edition (1974), and it has been determined that it belongs to the genus Alcaligenes. No known microorganism of genus Alcaligenes is described in the Bergey's manual which has the above microbiological characteristics, and moreover, the present strain differs from the Alcaligenes sp. PL-266 Meito strain disclosed in the earlier application cited above. Hence, the present strain has been named Alcaligenes sp. PL-679 Meito.

Table 1 below summarizes the main differences between Alcaligens sp. PL-679 Meito strain useful for the production of the microbial lipase of the invention and PL-266 Meito strain disclosed in the earlier application.

TABLE 1

| Characteristics | PL-266 Meito strain | PL-679 Meito strain (used in this invention) |
| --- | --- | --- |
| Nutrient agar colony | entire, greyish white or greyish yellow | lacerate, yellowish brown or brown |
| Nutrient gar slant | greyish white or greyish yellow | orange or yellowish brown |
| Nutrient broth | not turbid with no pellicle | turbid with pellicle |
| Gelatin stab | crateriform becoming stratiform | no liquefaction |
| Litmus milk | peptonization | no peptonization |
| Nitrate reduction | negative | positive |
| Hydrogen sulfide production | positive (weak) | positive |
| OF test | oxidative | not oxidative and not fermentative |
| Sugar assimilation | | |
| L-arabinose | positive | negative |
| D-xylose | " | " |
| D-glucose | " | " |
| D-mannose | " | " |
| D-galactose | " | " |
| inositol | " | " |
| maltose | " | " |
| sucrose | " | " |
| lactose | " | " |
| trehalose | " | " |
| D-sorbitol | " | " |
| mannitol | " | " |

TABLE 1-continued

| Characteristics | PL-266 Meito strain | PL-679 Meito strain (used in this invention) |
| --- | --- | --- |
| GC content of DNA | 74.2 mole % | 66.7 mole % |

The microbial lipase not described in the literature and having the characteristics (i) to (v) can be prepared as follows:

A microorganism belonging to the genus Alcaligenes, which has the ability to produce the microbial lipase having the characteristics (i) to (v) described hereinabove, is aerobically cultivated in a nutrient culture medium containing carbon and nitrogen sources and minerals at a temperature of about 5° to about 40° C., preferably about 10° to about 40° C. and a pH of about 5.5 to about 11, preferably about 6 to about 10, and the microbial lipase is recovered from the resulting culture broth.

According to this invention, there is also provided a biologically pure culture of Alcaligenes sp. PL-679 Meito which has the characteristics identified as FERM-P No. 3783, ATCC 31371 and DSM 1239 and has the ability to produce a microbial lipase capable of being activated with bile salts and having the characteristics (i) to (v) described hereinabove by aerobic fermentation in a nutrient culture medium containing carbon and nitrogen sources and minerals at a pH of about 5.5 to about 11, preferably about 6 to about 10, and a temperature of about 5° to about 40° C., preferably about 10° to about 40° C.

The carbon source, nitrogen source and minerals may be any materials which are ordinarily used in cultivating microorganisms.

The carbon source includes, for example, glucose, fructose, maltose, soluble starch, starch, dextrin, molasses, glycerol, oils and fats, wheat bran, lactose, and surcose. The nitrogen sources are organic or inorganic nitrogen-containing compounds such as soybean powder, defatted soybean powder, cotton seed residue, corza residue, peptone, meat extract, yeast extract, gluten, corn steep liquor, Casamino acid, urea, ammonium salts, and nitrate salts. Examples of the mineral are phosphate salts, magnesium salts, iron salts, potassium salts, sodium salts, and calcium salts. If desired, various other organic or inorganic substances useful for the growth of microorganisms or enzyme production, such as silicon oils, antiamers, vitamins and phosphorus-containing compounds, can be added to the culture medium.

By incorporating a nonionic surface active agent into the nutrient culture medium in the present invention, the amount of the microbial lipase produced can be conveniently increased. The output of the microbial lipase of the invention can be also increased by using salts capable of giving an iron ion, such as iron chloride or iron sulfate, in conjunction with sodium salts of organic acids such as sodium acetate or sodium citrate.

The amount of the nonionic surface-active agent to be used is about 0.01 to about 2% by weight based on the weight of the nutrient culture medium. Examples of the non-ionic surfactant are sorbitan alkyl esters, polyoxyethylene sorbitan alkyl esters, polyoxyethylene alkyl ethers, polyoxyethylene alkylaryl ethers, polyoxyethylene alkyl esters, a polyoxyethylene/polyoxypropylene copolymer, and fatty acid monoglycerides.

The cultivation is carried out under aerobic conditions, and either a submerge or surface cultivating technique can be used. Usually, however, the submerge culture is suitable. For commercial operation, it is advantageous to perform submerge cultivation under aeration and stirring. A desirable method is to perform a small-scale pre-cultivation, and inoculate the resulting culture broth into a culture medium for main cultivation.

The cultivating conditions somewhat vary according, for example, to the type of the strain used, and the composition of the culture medium. It is recommendable to select conditions which would be most advantageous for the production of the lipase as a final product. The cultivation temperature is generally about 5° to 40° C., preferably about 10° to about 40° C. Temperatures of 20° to 30° C. are especially preferred. The cultivation period differs according to the conditions, but is usually about 1 to about 4 days. The cultivation may be terminated at a time when the amount of lipase accumulated reaches a maximum. The pH of the culture medium may range from weak acidity to alkalinity at the time of preparing the culture medium. Usually, it is not particularly necessary to adjust the pH. The pH of the culture medium is generally about 5.5 to about 11, preferably about 6 to about 10, more preferably about 7 to about 10. The cultivation can be performed while adjusting the pH to the aforesaid ranges as required.

Recovery of the microbial lipase of this invention from the resulting culture broth can be performed by known procedures used for the separation and purification of lipase. Specifically, in the case of surface culture, the culture broth is extracted with water or another extracting agent to form an extract. In the case of submerge culture, the microbial cells or solids are separated from the culture broth by known filtration or centrifugation to obtain an extract or filtrate. The extract or filtrate can be used either as such or after concentration. By treating the extract, filtrate or its concentrated product by known means such as precipitation, spray drying or lyophilization, the microbial lipase of this invention can be obtained in the form of solid product.

Suitable precipitating agents used in the precipitation method include, for example, soluble salts such as sodium chloride, ammonium sulfae and sodium sulfate, and hydrophilic organic solvents such as ethanol, methanol and acetone. Suitable stabilizing aids used in the spray drying method include maltodextrin, lactose, carboxymethyl cellulose, polyethylene glycol, skim milk, casein, sorbitol and sodium chloride.

Furthermore, the lipase product of this invention having the desired purity and a lipase potency can be recovered by one or more of known purifying techniques such as an adsorption and eluting method using ion exchange resins, calcium phosphate gel, alumina or bentonite; a molecular sieve method using Sephadex, or biogel; a chromatographic method using cellulose or Sephadex ion exchanger; a precipitating method using a protein precipitant such as tannin and calcium salts; an isoelectric precipitating method; a dialysis method; and an electrophoretic method.

To the best of the knowledges of the present inventors, the microbial lipase of this invention characterized by having (i) an optimal pH for activity of about $9 \pm 0.5$,
(ii) an optimal temperature for activity of about 40° C. to about 48° C.,
(iii) a lipase activity to be activated by bile salts,
(iv) a cholesterol esterase activity, and
(v) a molecular weight of about $30 \times 10^4$ to about $40 \times 10^4$ has not been described in the literature. Lipases (I and II fractions) disclosed in our earlier application (Japanese Laid-Open Patent Publication No. 21387/77) are most similar to the novel microbial lipase of the present invention. The microbial lipase of this invention can, first of all, be clearly distinguished from the lipases I and II in regard to the characteristics (ii), (iv) and (v) described above, and also shows different activity inhibiting characteristics. Table 2 summarizes the characteristics of the microbial lipase of this invention in comparison with those of the lipases I and II in our earlier application.

TABLE 2

| Characteristics | Lipase of the invention | Lipase of Japanese Laid-Open Patent Publication No. 21387/77 | |
| --- | --- | --- | --- |
| | | Lipase I | Lipase II |
| Lipase activity | + | + | + |
| Cholesterol esterase activity | + | − | − |
| Lipoprotein lipase activity | + | + | + |
| Optimal pH for activity | $9 \pm 0.5$ | $9 \pm 0.5$ | $10 \pm 0.5$ |
| Optimal temperature for activity | 40–48° C. | 70–75° C. | 70–80° C. |
| Molecular weight | $34 \times 10^4$–$37 \times 10^4$ | $18 \pm 1 \times 10^4$ | $3.2 \times 10^4$–$3.7 \times 10^4$ |
| Activity inhibition by $Hg^{++}$, $Fe^{++}$, $Zn^{++}$, $Sn^{++}$, $Cd^{++}$ or $Cr^{+++}$ (concentration, $10^{-3}$ mole) | Inhibited (more than 50%) | Not inhibited | Inhibited by $Cd^{++}$ (10–20%), but not by the other metal ions |
| Activity inhibition by sodium ascorbate (concentration, $10^{-2}$ mole) | Inhibited (more than 50%) | Not inhibited | Not inhibited |
| Activity inhibition by monoiodoacetic acid (concentration, $10^{-3}$ mole) | Inhibited (more than 50%) | Not inhibited | Not inhibited |

The enzymological characteristics of the microbial lipase of this invention are described in detail hereinbelow. In the present application, the measurement and determination of these characteristics are performed as follows:

Preparation of specimens

Mycela and other solids are separated by filtration from the culture broth. The filtrate is cooled to about 5° C., and ammonium sulfate is added with stirring to this filtrate to 40% saturation. The mixture is allowed to stand at about 5° C. for 24 hours. The precipitated enzyme is collected, and dialyzed in flowing water at about 18° C. for 2 days using a cellophane dialytic membrane. The dialyzate is further dialyzed at about 5° C. for 24 hours against a tris-buffer solution (concentration 0.01 mole; pH 9.0). The dialyzed enzyme solution is applied at about 5° C. onto a column of DEAE-cellulose ion exchanger equilibrated sufficiently by a tris-buffer (concentration 0.01 mole; pH 9.0). The columm is then washed with a tris-buffer (concentration 0.01 mole; pH 9.0), and eluted with a tris-buffer (0.01 mole, pH 9.0) by gradually increasing the concentration of sodium chloride in the buffer to 0.4 mole. The activity of the effluent is measured, and active fractions are collected. The active fractions are then placed in a cellophane dialytic membrane, and concentrated by using polyethylene glycol powder. The concentrate is dialyzed in flowing water at about 18° C. for 24 hours in the same manner as described above, and further dialyzed against a tris-buffer. The dialyzate is chromatographed again and the resulting active fractions are again concentrated as described above. The concentrate is then centrifuged to remove solids. The enzyme solution obtained is gel-filtered by passing it through a column of Sephadex G-200 using the same tris-buffer as above, and the active fractions are collected. The resulting active fractions are concentrated and centrifuged in the same way as above, and the resulting enzyme solution is gel-filtered in the same way as above using a column of Sepharose 4B. Thus, a purified specimen is obtained.

Using the purified specimen, the characteristics (i) to (vii) are measured and determined by the following methods.

(iv) Cholesterol esterase activity

The measurement of cholesterol esterase activity is performed in accordance with the procedure described in Leschroue et al.: Z. Klin. Chem. Klim. Biochem., 12, 403 (1974).

(v) Molecular weight

The measurement and calculation of the molecular weight are performed in accordance with the method disclosed in P. Andrews: Biochem. J. 91, 222 (19640). A column, 2.5×100 cm in size, is packed with a gel of Sephadex G-200, and as a standard substance, catalase (molecular weight 240,000) and ferritin (molecular weight 540,000) are used. A 1/100 M tris-HCl buffer (pH 8.7) is used as an eluting buffer.

(vi) Lipoprotein lipase activity

The lipoprotein lipase activity is determined by the method of Saiki et al. [Agr. Biol. Chem. 32, 1459 (1968]. As a human serum, Human Plasma, fresh, lyophilized (Miles Laboratories, Inc.) is used, and Fatgen (a product of Dainippon Pharmaceutical Co., Ltd.) is used as an oil and fat.

(vii) Activity inhibition by sodium ascorbate and monoiodoacetic acid

An aqueous solution of the lipase sample (about 3 units/ml) is contacted with each of the inhibiting agents at 37° C. for 10 minutes, and the lipase activity is measured. The concentration of sodium ascorbate is $10^{-2}$ mole, and the concentration of monoiodoacetic acid is $10^{-3}$ mole.

The method of determining the characteristics (i), (ii) and (iii) is described below with regard to the enzymological characteristics of the microbial lipase of this invention.

(1) Mode of action

The microbial lipase of this invention is an enzyme which hydrolyzes oils and fats to glycerol and fatty acdis, and yields large quantities of monoglycerides as intermediates during the hydrolysis.

(2) Substrate specificity

The lipase activities of the present microbial lipase on oils and fats and various esters are shown in Table 3 below in terms of percentages based on the activity on olive oil.

TABLE 3

| Substrate | Relative activity (%) |
|---|---|
| Olive oil | 100 |
| methyl n-butyrate | 1 |
| Methyl n-ceproate | 3 |
| Methyl n-caprylate | 6 |
| Methyl n-caprate | 6 |
| Methyl laurate | 6 |
| Methyl myristate | 7 |
| Methyl palmitate | 34 |
| Methyl stearate | 33 |
| Methyl oleate | 18 |
| Tributyrin | 60 |
| Tricaproin | 52 |
| Tricaprylin | 123 |
| Tricaprin | 100 |
| Triolein | 141 |
| Monolein | 86 |
| Monolaurin | 40 |
| Dilaurin | 75 |
| Trilaurin | 128 |
| Span 85 | 29 |
| Tween 85 | 20 |
| Castor oil | 85 |
| Buffer fat | 53 |

It is seen from Table 3 that the microbial lipase of this invention acts not only on glycerol esters of higher fatty acids such as natural oils and fats, but also on water-soluble esters such as Tween 85.

The microbial lipase of this invention also acts on cholesterol esters of fatty acids to convert them into fatty acids and cholesterol.

(3) Optimal pH range for stability [determination of characteristic (i)]

Figure 1:
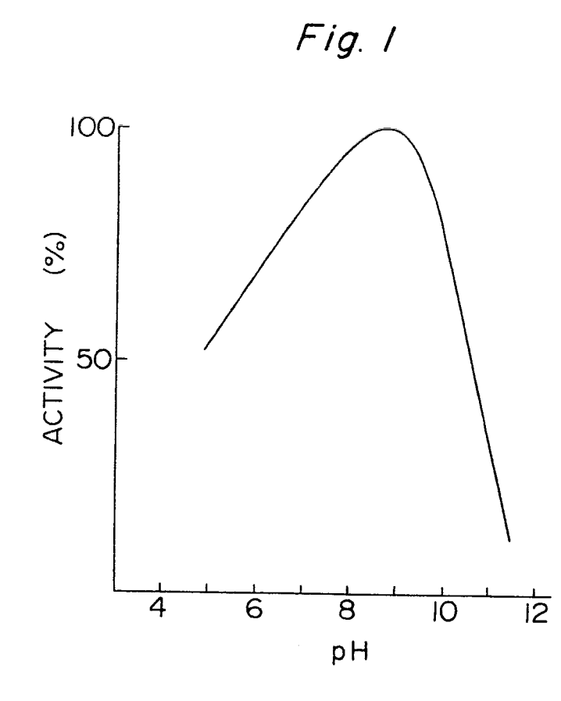

The present lipase is dissolved in a concentration of 2.5 to 5 U/ml, and the optimal pH is examined. The results are shown in FIG. 1 which shows that the maximum activity is noted at a pH of about 9±0.5.

Figure 2:
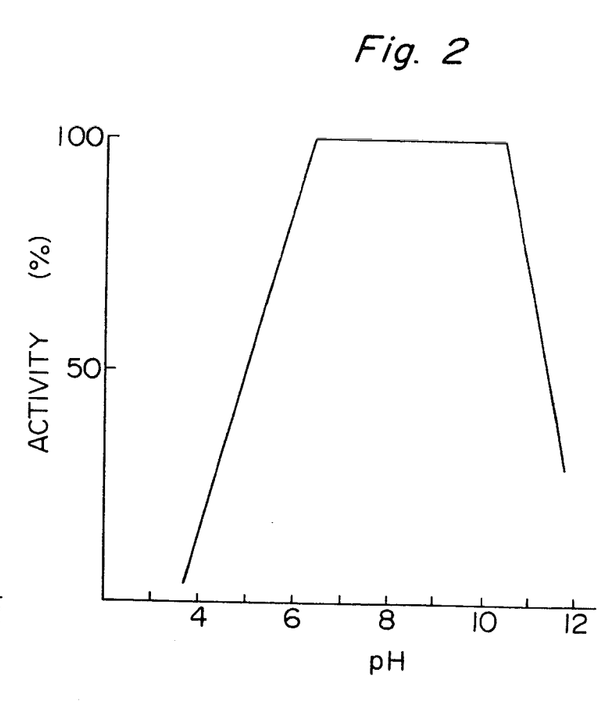

The present lipase is maintained in a concentration of 50–100 U/ml in buffers of various pH values at 5° C. for 24 hours, and then the pH is adjusted to 8.6 with a glycine buffer. The residual lipase activity is measured, and shown in FIG. 2. The lipase is thus found to be substantially stable at a pH in the range of about 6.5 to about 10.5. A McIlvaine buffer (1/10 M citric acid, 1/5 M $Na_2HPO_4$) is used for a pH range of 2.5 to 8.0; a 1/5 M tris-maleate buffer, for a pH range of 5.5 to 8.5; a 1/10 M $Na_2CO_3$—$H_3BO_4$—KCl buffer, for a pH range of 8.0 to 10.5; and a 1/5 $Na_2HPO_4$—NaOH, for a pH range of 11 to 12.

(4) Suitable activity temperature [determination of the characteristic (ii)]

Figure 3:
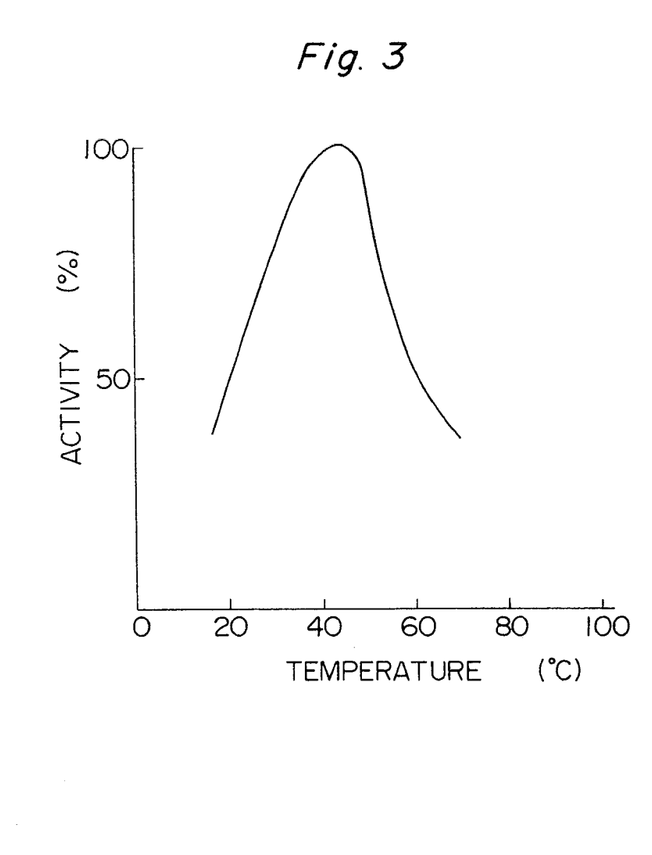

The suitable activity temperature range of the present lipase is shown in FIG. 3, and the optimal temperature range is about 40° to about 48° C. The method of measurement is as follows:

The reaction substrate used in the activity assay method to be described hereinbelow is pre-heated at various temperatures for 10 minutes, and 1 ml of an enzyme solution (concentration, 0.01 mg/ml) is added and reacted for 10 minutes at the temperature used in the pre-heating. The activities at the various temperatures are expressed as percentages based on the activity of the lipase at 45° C.

(5) Inactivation by pH and temperature conditions

Figure 4:
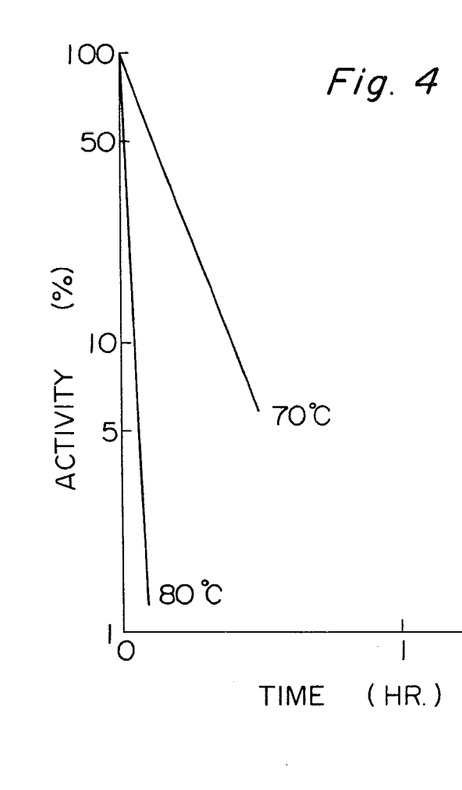

The lipase is dissolved in water in a concentration of 4 U/ml, and the solution is maintained at a temperature of 70° to 80° C. Changes in the activity of the lipase are examined periodically by the assay method to be described hereinbelow. The results are shown in FIG. 4. It is seen that by heat-treatment at 80° C. for 30 minutes, the lipase is almost completely inactivated.

The lipase is dissolved in water in a concentration of 25-50 U/ml, and mixed with an equal amount of a McIlvaine buffer (pH 3.0) and a ¼ M $Na_2HPO_4$—NaOH buffer (pH 12.0), respectively. Each of the mixtures is maintained at 37° C., and then sampled at predetermined times. The sampled mixtures are each diluted to 5 times with a 1 M glycine buffer (pH 8.7), and the activity of the lipase is measured. At a pH of 3.0, more than 95% of the lipase activity is lost in 10 minutes; at a pH of 12.0, more than 95% of the lipase activity is lost in 120 minutes.

(6) Inhibition

The lipase in a concentration of about 3 U/ml is contacted with various inhibiting reagents at 37° C. for 10 minutes, and then the lipase activity is measured. When the concentration of the inhibiting reagent is $10^{-3}$ mole, the activity of the lipase is seen to be inhibited more than 50% by $Hg^{++}$, $Fe^{+++}$, $Zn^{++}$, $Sn^{++}$, $Cd^{++}$ and $Cr^{+++}$. Furthermore, inhibition is more than 50% with $10^{-2}$ mole of sodium ascorbate; about 100% with $10^{-3}$ mole of monoiodoacetic acid; about 10 to about 20% with $10^{-2}$ mole of potassium ferricyanide, pyrophosphate salts, sodium azide, and sodium ethylenediaminetetraacetate; about 95% with $10^{-2}$ mole of iodine; and about 70% with $10^{-2}$ mole of ethoxyformic anhydride.

(7) Activation [method of determination of characteristic (iii)]

In the lipase activity assay method to be described in paragraph (8) below, various bile salts are dissolved in distilled water, and the lipase activity is measured. As shown in Table 4, the present lipase is evidently activated with bile salts.

TABLE 4

| Bile salts | Concentration of bile salt (%) | | | |
|---|---|---|---|---|
| | 0.2 | 0.4 | 0.6 | 0.8 |
| Taurocholate | 221 | 229 | 224 | 226 |
| Glycocholate | 218 | 221 | 232 | 224 |
| Cholate | 197 | 221 | 211 | 229 |
| Desoxycholate | 289 | 300 | 305 | 303 |

The activities shown in the above table are percentages based on the lipase activity in the absence of a bile salt.

(8) Assay of activity (a) Composition of a reaction mixture:

Enzyme solution: 1.0 ml
Glycine buffer (1 mole, pH 8.7): 2.0 ml
Olive oil emulsion: 2.5 ml
Distilled water: 0.5 ml The olive oil emulsion is prepared by adding 20 g of olive oil to 180 ml of a 10% aqueous solution of gum arabic, homogenizing the mixture at 11,000 r.p.m. for 15 minutes while it is cooled to 5°–10° C., and adjusting the pH of the homogenized mixture to 8.7.

(b) Procedure:

The reaction mixture is placed in a 25 ml glass stopper tube, and reacted exactly for 10 minutes at 37° C. Then, the reaction is stopped by adding 1 ml of 2 N sulfuric acid, and 15 ml of a mixture of n-heptane and isopropanol in a ratio of 11:4 is added. The mixture is vigorously shaken for 30 seconds, and allowed to stand for more than 30 minutes. 5 ml of the upper layer is collected, and titrated under nitrogen gas with a 0.01 N ethanolic potassium hydroxide solution using Thymol Blue as an indicator. 2 N sulfuric acid solution is added to a reaction mixture having the same composition as above, and then the enzyme solution is added. The mixture is treated in the same way as above, and the resulting product is titrated with a potassium hydroxide solution, and the measured value obtained is substracted from the measured value obtained above. The amount of fatty acid liberated is calculated from the resulting titration value with reference to the standard line prepared by using a known amount of palmitic acid.

One lipase unit is defined as the enzyme amount which liberates 1 μmole of fatty acid in one minute under the assay conditions described above.

(9) Method of purification

The lipase of the invention can be purified by salting out, cellulose ion exchange chromatography, and gel filtration either alone or in suitable combinations. One embodiment is shown in Example 5.

As described above, the properties of the present lipase are very similar to those of pancreatic lipase of an animal in optimal pH (in alkalinity) for activity and activation with bile salts.

The lipase of the invention also has the ability to decompose cholesterol ester (i.e., a cholesterol esterase activity). It has not been known heretofre that a lipase having such a property is produced by a microorganism of the genus Alcaligenes.

Table 5 summarizes the characteristics of the lipase of this invention in comparison with those of known microbial lipases capable of being activated with bile salts.

TABLE 5

| Microorganism | | Optimal pH | Optimal temperature (°C.) | Factor of activation by bile salts | Cholesterol esterase | Molecular weight | Lipoprotein lipase | Inhibition by reagents | Literature references |
|---|---|---|---|---|---|---|---|---|---|
| Chromobacterium viscosum var. paralipolytica | | 7.0 | 65 | 1.5 | — | 120,000 30,000 | No | — | Agr. Biol. Chem. 37, 999 (1973); Japanese Patent Publication No. 29787/71; J. Biochem. 81, 1639 (1977) |
| Pseudomonas stutzeri (ATCC 19154) | | 9–9.5 | — | 6–10 | — | — | — | — | Japanese Patent Publication No. 10754/69 |
| Phycomyces sp. | | 6–7 | 40 | 2 | — | 26,500±500 | Yes | — | Japanese Patent Publication No. 17559/75; Abstracts of Papers at the 1974 Annual Meeting of the Agricultural Chemical Society of Japan; Abstracts of Papers at the 1977 Meeting of the Central and Western Divisions of the Agricultural Chemical Society of Japan |
| Mucor javanicus | | 7.0 | — | 2–5 | — | — | — | — | Yakuzaigaku ("Pharmaceutical Science") 27, 314 (1967); Eisei Kagaku ("Hygienic Chemistry") 13, 257 (1967) |
| Alcaligenes sp. PL-266 Meito | I | 8.5–9.5 | 70–75 | 2 | No | 180,000 ±10,000 | Yes | Not inhibited by ascorbic acid | Japanese Laid-Open Patent Publication No. 21387/77 |
| | II | 9.5–10.5 | 70–80 | 2 | No | 32,000–37,000 | Yes | and monoiodoacetic acid | |
| Alcaligenes sp. PL-679 Meito (used in this invention) | | 8.5–9.5 | 40–48 | 2 | Yes | 300,000–400,000 | Yes | Inhibited by ascorbic acid and monoiodoacetic acid | |

Referring to Table 5, lipase produced by *Chromobacterium viscosum, Phycomyces sp.* and *Mucor javanicus* are similar to the lipase of the invention in regard to the factor of activation by bile salts, but the optimal pH values for these lipases are in the neutral region and thus differ from that for the microbial lipase of the present invention. The lipase produced by *Pseudomonas stutzeri* differs from the lipase of the invention in regard to the factor of activation with bile salts, and its optimal pH curve differs considerably from that of the lipase of the invention (see FIG. 1).

The lipase of the invention also differs from lipase produced by *Alcaligenes sp.* PL-266 Meito discovered previously by the present inventors, in regard to the optimal temperature for activity, and the possession of cholesterol esterase activity. As shown in Table 2, there are also differences, for example, in molecular weight and inhibition by metal ions.

The microbial lipase of the invention can be used in a wide variety of applications, for example, as medicines and diagnostic reagents, and also for producing fatty acids, glycerol, and monoglycerides, enhancing milk flavor, improving the quality of bread and cookies, utilization in sewage treatment, and addition to leather tanning agents, hair rinsing agents, bath agents, face washing agents, and to feeds.

Furthermore, since the microbial lipase of the invention has an optimal pH in the alkaline region, and can be activated with bile salts, it has the advantage that when orally administered as a digestant for example, it is activated with bile salts in the intestinal juice and shows increased activity. The microbial lipase of the invention well decomposes lipoprotein in food because it has a lipoprotein lipase activity. When the lipase of the invention is utilized as a digestant, it may be orally administered in a dose of 1000 to 8000 U/day, for example. As a diagnostic reagent, the cholesterol level in the blood can be determined by using 0.1 to 2.0 U of cholesterol esterase in a single test. Furthermore, by using 100 to 1000 U of lipoprotein lipase in a single test, the triglyceride level in the blood can be determined.

When the lipase of the present invention was administered to rats in a dose of 2.5 and 5.0 g/kg respectively for one month and in a dose of 2.5 g/kg for three months by a natural in-take method to determine its subacture toxicity. No change was noted in the general behaviors, feces, urine, blood examination, autopsy, and the weight of organs. No significant change was noted either in histological examination.

The following Examples illustrate the present invention in greater detail.

EXAMPLE 1

500 ml shaking flasks were each filled with 50 ml of a liquid culture medium containing 3% of soybean powder, 1% of defatted soybean powder, 1% of corn steep liquor, 0.5% of dipotassium phosphate and 0.25% of sodium nitrate and adjusted to pH 8.0, and the culture media were sterilized with steam at 120° C. for 15 minutes.

*Alcaligenes sp.* PL-679 Meito (FERM-P No. 3783 strain) was inoculated into the media, and cultivated with shaking at 30° C. for 40 hours. The culture broth was centrifuged, and the lipase activity of the supernatant liquid was measured and found to be 50 U/ml. Ammonium sulfate was added to 50% saturation to 100 ml of the culture broth. The resulting precipitate was collected and dried to afford 1.5 g of a crude enzyme powder having a lipase activity of 2560 U/g.

EXAMPLE 2

The procedure of Example 1 was repeated except that 0.5% of sorbitan oleyl ester was added to the culture medium described in Example 1. The lipase activity of the supernatant liquid of the culture broth was found to be 351 U/ml.

An enzyme powder in an amount of 1.4 g was collected in the same way as in Example 1 from the resulting culture broth. The lipase activity of this powder was 16,000 U/g.

EXAMPLE 3

A liquid culture medium containing 3% of soybean powder, 0.5% of defatted soybean powder, 0.5% of corn steep liquor, 0.1% of wheat starch, 0.2% of dipotassium phosphate, 0.5% of polyethylene stearyl ether, 1.0% of sodium nitrate and 0.075% of silicone was adjusted to pH 9.5. 50 ml of the culture medium was filled in a 500 ml shaking flask, and steam-sterilized at 120° C. for 15 minutes. *Alcaligenes sp.* PL-679 Meito (FERM-P No. 3783 strain) was inoculated, and cultivated with shaking at 30° C. for 40 hours, and the culture broth was filtered. The filtrate was found to have a lipase activity of 500 U/ml, a cholesterol esterase activity of 3.7 U/ml and a lipoprotein lipase activity of 155 U/ml. To 500 ml of the filtrate was added cold acetone to a concentration of 80%. The precipitate was collected, washed with cold acetone, and dried in vacuo at room temperature to afford 12.5 g of a crude enzyme powder. The powder had a lipase activity of 13,200 U/g, a cholesterol esterase activity of 99 U/g, and a lipoprotein lipase activity of 4,100 U/g.

EXAMPLE 4

To 15 liters of the culture medium described in Example 3 were added 0.4% of sodium citrate and 0.028% of ferrous sulfate, and the mixture was put into a 30-liter jar fermentor. As an antifoamer, 5 g of a silicone oil was added, and the mixture was steam-sterilized.

*Alcaligenes sp.* PL-679 Meito (FERM-P No. 3783 strain) was inoculated into the culture medium so prepared, and cultivated under aeration and stirring at 24° C. for 38 hours. The culture broth was filtered to obtain 12.0 liters of a filtrate having a lipase activity of 800 U/ml. The absorbance of this filtrate at 280 nm was 100. The filtrate had a cholesterol esterase activity of 6 U/ml, and a lipoprotein lipase activity of 250 U/ml.

Ammonium sulfate was added to 2.4 liters of this filtrate to 40% saturation, and the mixture was allowed to stand at 5° C. for 24 hours. The supernatant liquid was decanted off, and the precipitate was collected by centrifugal separation. About 73% lipase activity were recovered in the precipitate that formed by the addition of ammonium sulfate.

EXAMPLE 5

The precipitate obtained in Example 4 by addition of ammonium sulfate was put into a cellophane tube, and dialyzed in flowing water for 2 days and further at 5° C. for 24 hours against a 0.01 M tris-buffer having a pH of 9.0. Filtration of the dialyzate afforded 1.3 liters of an enzyme solution having a lipase activity of 1,020 U/ml and an absorbance at 280 nm of 28.5.

The enzyme solution was applied to a column of a DEAE-cellulose ion exchanger sufficiently equlibrated with a 0.01 M tris-buffer having a pH of 9.0. The adsorbed enzyme solution was washed with the same buffer, and eluted with a tris-buffer (0.01 mole, pH 9.0) by gradually increasing the concentration of sodium chloride in the buffer to 0.4 mole. Fractions having a lipase activity were eluted when the concentration of NaCl was within the range of 0.05 to 0.2 mole. Their activities were measured, and the active fractions were collected. The collected fractions were concentrated, and gel-filtered through Sephadex G-200 and Sepharose 4B in this order, and the active fractions were collected.

The active fractions collected were again dialyzed, and then re-chromatographed on a column of DEAE-cellulose. The active fractions were eluted by the concentration gradient method using sodium chloride. The fractions having a lipase activity were concentrated, and lyophilized to form 293 g of a purified lipase powder. A 0.1% aqueous solution of the purified enzyme powder had an absorbance at 280 nm of 0.43. The enzyme powder had a lipase activity of 890 U/mg, a cholesterol esterase activity of 6.6 U/mg and a lipoprotein lipase activity of 275 U/mg. The lipase had an optimal pH range of about $9\pm0.5$, and an optimal temperature of about 45° C. It could be activated to about two times its original activity with 0.2% sodium taurocholate. The molecular weight was about $35\times10^4$. The activity inhibition of the lipase by sodium ascorbate was about 52%, and that by monoiodoacetic acid was about 98%.

EXAMPLE 6

50 ml of a liquid culture medium containing 3% of soybean powder, 1% of fructose, 0.2% of potassium phosphate, 1% of sodium nitrate, 0.6% of sodium citrate, 0.03% of $FeSO_4.7H_2O$, 0.5% of polyethylene glycol stearyl ether and 0.2% of an antifoamer was filled into a 500 ml shaking flask, and steam-sterilized at 120° C. for 15 minutes.

*Alcaligenes sp.* PL-679 Meito FERM-P No. 3783 strain was inoculated into the sterilized culture medium, and cultivated with shaking at 25° C. for 42 hours. The culture broth was centrifuged, and the enzyme activity of the supernatant liquid was measured. It was found to have a lipase activity of 2,000 U/ml, a cholesterol esterase activity of 15 U/ml and a lipoprotein lipase activity of 625 U/ml. To 100 ml of the resulting supernatant liquid was added 400 ml of cold acetone. The resulting precipitate was collected, dehydrated with acetone, and vacuum-dried at 25° C. to afford 1.8 g of an enzyme powder which had a lipase activity of 77,000 U/g, a cholesterol esterase activity of 585 U/g and a lipoprotein lipase activity of 24,000 U/g.

What we claim is:
1. A microbial lipase which has
    (i) an optimal pH for activity of about $9\pm0.5$,
    (ii) an optimal temperature for activity of about 40° C. to about 48° C.,
    (iii) a lipase activity to be activated by bile salts,
    (iv) a cholesterol esterase activity, and
    (v) a molecular weight of about $30\times10^4$ to about $40\times10^4$.

2. The microbial lipase of claim 1 which further has (vii) a lipoprotein lipase activity.

3. The microbial lipase of claim 1 which has a cholesterol esterase activity of at least 300 U/g in the crude state and at least 6,600 U/g in the purified state.

4. The microbial lipase of claim 1 which further shows (viii) an activity inhibition of at least about 50% by sodium ascorbate in a concentration of $10^{-2}$ mole and monoiodoacetic acid in a concentration of $10^{-3}$ mole.

5. The microbial lipase of claim 1 which is produced by a microorganism of genus Alcaligenes having the ability to produce the microbial lipase described in claim 1.

6. The microbial lipase of claim 5 wherein the microorganism has characteristics that permit its identification as *Alcaligenes sp.* PL-679 Meito strain.

7. The microbial lipase of claim 6 wherein the microorganism is *Alcaligenes sp.* PL-679 Meito FERM-P No. 3783 *Alcaligenes sp.* PL-679 Meito ATCC 31371 strain.

8. A process for preparing the microbial lipase of claim 1, which comprises aerobically cultivating a microorganism of the genus Alcaligenes having the ability to produce the microbial lipase of claim 1 in a nutrient culture medium containing a carbon source, a nitrogen source and minerals at a pH of about 5.5 to about 11 and a temperature of about 5° to about 40° C., and recovering the microbial lipase from the resulting culture broth.

9. The process of claim 8 wherein the culture medium further contains a nonionic surface-active agent.

10. The process of claim 9 wherein the amount of the nonionic surface-active agent is about 0.01 to about 2% by weight based on the weight of the nutrient culture medium.

11. A biologically pure culture of *Alcaligenes sp.* PL-679 Meito, ATCC 31371 strain which has the ability to produce a microbial lipase capable of being activated by bile salts and characterized by having
- (i) an optimal pH for activity of about 9±0.5,
- (ii) an optimal temperature for activity of about 40° C. to about 48° C.,
- (iii) a lipase activity to be activated by bile salts,
- (iv) a cholesterol esterase activity, and
- (v) a molecular weight of about $30 \times 10^4$ to about $40 \times 10^4$, by aerobic fermentation in a nutrient culture medium containing a carbon source, a nitrogen course and minerals at a pH of about 5.5 to about 11 and a temperature of about 5° to about 40° C.

* * * * *